United States Patent
Wolf et al.

(10) Patent No.: US 11,183,291 B2
(45) Date of Patent: Nov. 23, 2021

(54) GENERATING PERSONALIZED NUTRITIONAL RECOMMENDATIONS USING PREDICTED VALUES OF BIOMARKERS

(71) Applicant: Zoe Limited, London (GB)

(72) Inventors: Jonathan Thomas Wolf, London (GB); George Hadjigeorgiou, London (GB); Richard James Davies, London (GB)

(73) Assignee: Zoe Limited, London (GB)

( * ) Notice: Subject to any disclaimer, the term of this patent is extended or adjusted under 35 U.S.C. 154(b) by 115 days.

(21) Appl. No.: 15/894,798

(22) Filed: Feb. 12, 2018

(65) Prior Publication Data
US 2019/0252058 A1    Aug. 15, 2019

(51) Int. Cl.
| G09B 19/00 | (2006.01) |
| G16H 20/60 | (2018.01) |
| G09B 5/02  | (2006.01) |
| G16H 50/70 | (2018.01) |

(52) U.S. Cl.
CPC ............... *G16H 20/60* (2018.01); *G09B 5/02* (2013.01); *G09B 19/0092* (2013.01); *G16H 50/70* (2018.01)

(58) Field of Classification Search
CPC .................................................. G09B 19/0092
USPC ......................................................... 434/127
See application file for complete search history.

(56) References Cited

U.S. PATENT DOCUMENTS

| 7,999,674 B2 | 8/2011 | Kamen |
| 8,690,578 B1 | 4/2014 | Nusbaum et al. |
| 9,011,153 B2 | 4/2015 | Bennett et al. |
| 2003/0091964 A1 | 5/2003 | Yeager |
| 2009/0275002 A1 | 11/2009 | Hoggle |
| 2011/0091842 A1 | 4/2011 | Dugan |

(Continued)

FOREIGN PATENT DOCUMENTS

| WO | WO0205702 | 1/2002 |
| WO | WO2008154759 A1 | 12/2008 |

(Continued)

OTHER PUBLICATIONS

Anonymous, "Glucose meter—Wikipedia", retrieved on Oct. 30, 2019 at <<https://en.wikipedia.org/w/index.php?title=Glucosemeter&oldid=851737873#Noninvasive_meters>>, Jul. 24, 2018, 15 pages.

(Continued)

*Primary Examiner* — Kesha Frisby
(74) *Attorney, Agent, or Firm* — Lee & Hayes, P.C.

(57) ABSTRACT

Techniques are disclosed herein for generating personalized nutritional recommendations using predicted values of target biomarkers. Using the technologies described herein, a programmatic analysis is performed on different data to predict values of target biomarkers that are associated with an individual. Personalized nutritional recommendations are then generated, using the predicted values, and provided to the individual. The predictions are based on data that is associated with the individual, such as microbiome data, ketone data, glucose data, nutritional data, questionnaire data, and the like. A prediction service can utilize a machine learning mechanism to generate the predicted value of the target biomarkers. A nutrition service utilizes the predicted value of the target biomarkers when generating the personalized nutritional recommendations.

24 Claims, 7 Drawing Sheets

(56) References Cited

U.S. PATENT DOCUMENTS

| | | |
|---|---|---|
| 2013/0216982 A1 | 8/2013 | Bennett et al. |
| 2015/0079551 A1 | 3/2015 | Egan |
| 2015/0093725 A1 | 4/2015 | Baarman et al. |
| 2015/0118659 A1 | 4/2015 | Meyer |
| 2015/0140523 A1 | 5/2015 | Dewan |
| 2015/0206450 A1 | 7/2015 | Wayman et al. |
| 2015/0294593 A1 | 10/2015 | Schoen et al. |
| 2015/0294594 A1 | 10/2015 | Pacione et al. |
| 2015/0371553 A1 | 12/2015 | Vento |
| 2016/0035248 A1 | 2/2016 | Gibbs |
| 2016/0042660 A1 | 2/2016 | Radovcic |
| 2016/0049091 A1 | 2/2016 | Omidi |
| 2016/0049092 A1 | 2/2016 | Barnett et al. |
| 2016/0063888 A1 | 3/2016 | McCallum et al. |
| 2016/0071423 A1 | 3/2016 | Sales et al. |
| 2016/0071432 A1 | 3/2016 | Kurowski et al. |
| 2016/0098942 A1 | 4/2016 | Messier |
| 2016/0140869 A1 | 5/2016 | Kuwahara et al. |
| 2016/0166195 A1 | 6/2016 | Radecka et al. |
| 2016/0232311 A1 | 8/2016 | Segal et al. |
| 2016/0253922 A1 | 9/2016 | Kremen et al. |
| 2016/0379520 A1 | 12/2016 | Borel et al. |
| 2019/0251861 A1 | 8/2019 | Wolf et al. |
| 2019/0362648 A1 | 11/2019 | Hadjigeorgiou et al. |
| 2019/0362848 A1 | 11/2019 | Wolf et al. |
| 2020/0065681 A1 | 2/2020 | Wolf et al. |
| 2020/0066181 A1 | 2/2020 | Hadjigeorgiou et al. |

FOREIGN PATENT DOCUMENTS

| | | |
|---|---|---|
| WO | WO2015166489 | 11/2015 |
| WO | WO2018031991 | 2/2018 |

OTHER PUBLICATIONS

Carson et al, "Challenges for measurement science and measurement practice: the collection and interpretation of home-monitored blood glucose data", Measurement, vol. 24, No. 4, Institute of Measurement and Control, Dec. 1, 1998, pp. 281-293.

Edelman et al, "Multisite Evaluation of a New Diabetes Selt-Test for Glucose and Glycated Protein (Fructosamine)", Diabetis Technology & Therapeutics, vol. 2, No. 2, Jan. 1, 200, pp. 233-238.

Kulkarni, "Comparision of Image Recognition APIs on Food Images", retrieved on Oct. 19, 2019 at <<https://byles.grubhub.com/https-medium-com-rohan-kulkarni comparison-of-image-recognition-apis-on-food-images-cddc9105fc33>>, pp. 1-9.

The PCT Search Report and Written Opinion dated Nov. 22, 2019 for PCT Application No. PCT/EP2019/072806, 15 pages.

The PCT Search Report and Written Opinion dated Nov. 8, 2019 for PCT Application No. PCT/EP2019/071801, 14 pages.

The PCT Search Report and Written Opinion dated Dec. 5, 2019 for PCT Application No. PCT/EP2019/072804, 14 pages.

Seeberg et al, "Development of a weable multisensor device enabling continuous monitoring of vital signs and activity", IEEE-EMBS International Conference on Biomedical and Health Informatics (BHI), IEEE, Jun. 1, 2014, pp. 213-218.

Tushuizen et al, "Postprandial lipid and apolipoprotein responses following three consecutive meals associate with liver fat content in type 2 diabetes and the metabolic syndrome", Atherosclerosis, vol. 211, No. 1, Elsevier, Amsterdam, NL, Feb. 10, 2010, pp. 308-314.

Von Niederhausem et al, "Validity of mobile electronic data capture in clinical studies: a pilot study in pediatric population", BMC Medical Research Methodology, vol. 17, No. 1, Dec. 1, 2017, 10 pages.

Wolcott et al, "Laboratory Medicine: A National Status Report Division of Laboratory Systems National Center for Preparedness, Detection, and Control of Infectious Diseases Centers for Disease Control and Prevention—The Lewin Group under Subcontract to Battelle Memorial Institute", retrieved on Nov. 25, 2019 at <<http://www.lewin.com/content/dam/Lewin/Resources/Site_Sections/Publications/39931>>, May 1, 2008, 385 pages.

Yun et al, "Smartphone-based point-of-care lipid blood test performance evaluation compared with a clinical diagnostic laboratory method", arxiv.org, Cornell University Library, Ithaca, NY, Apr. 19, 2018, 8 pages.

The PCT Search Report dated May 21, 2019, for PCT Application No. PCT/IB2019/051088, 11 pages.

The PCT Search Report dated May 21, 2019, for PCT Application No. PCT/IB2019/051089, 12 pages.

The PCT Search Report dated Sep. 3, 2019, for PCT Application No. PCT/EP2019/063330, 15 pages.

Non Final Office Action dated Jan. 10, 2020 for U.S. Appl. No. 15/894,776 "Generating Predicted Values of Biomarkers for Scoring Food" Wolf, 11 pages.

The International Preliminary Report on Patentability dated Mar. 11, 2021 for PCT Application No. PCT/EP2019/072804, 9 pages.

Office Action for U.S. Appl. No. 16/120,039, dated Mar. 22, 2021, Hadjigeorgiou, "Generating Personalized Food Recommendations from Different Food Sources", 12 pages.

Final Office Action dated Jul. 10, 2020 for U.S. Appl. No. 15/894,776, "Generating Predicted Values of Biomarkers for Scoring Food", Wolf, 6 pages.

Non Final Office Action dated Oct. 7, 2020 for U.S. Appl. No. 16/434,135, "Using at Home Measures to Predict Clinical State and Improving the Accuracy of at Home Measurements/Predictions Data Associated with Circadian Rhythm and Meal Timing", Wolf, 6 pages.

Non Final Office Action dated Dec. 10, 2020 for U.S. Appl. No. 15/987,699, "Improving the Accuracy of Measuring Nutritional Responses in a Non-Clinical Setting", Hadjigeorgiou, 12 pages.

Non Final Office Action dated Jul. 9, 2021 for U.S. Appl. No. 16/434,135, "Using at Home Measures to Predict Clinical State and Improving the Accuracy of at Home Measurements/Predictions Data Associated with Circadian Rhythm and Meal Timing", Wolf, 6 pages.

GENERATING PERSONALIZED NUTRITIONAL RECOMMENDATIONS USING PREDICTED VALUES OF BIOMARKERS

BACKGROUND

Today, individuals have a large variety of food choices. Determining healthy food choices for an individual can be challenging. Complicating the selection of food that is healthy for a user include factors that are personal to the user. Age, sex, weight, and the microbiome of an individual affect what foods an individual should select to eat. For example, while low carbohydrate food or low fat food may be beneficial for one individual, that same low carbohydrate or low fat food choice may not be beneficial for another individual. In many cases, an individual may try many different type of foods and nutritional plans in an attempt to find the nutritional plan and foods that works best for them.

DETAILED DESCRIPTION

Figure 1:
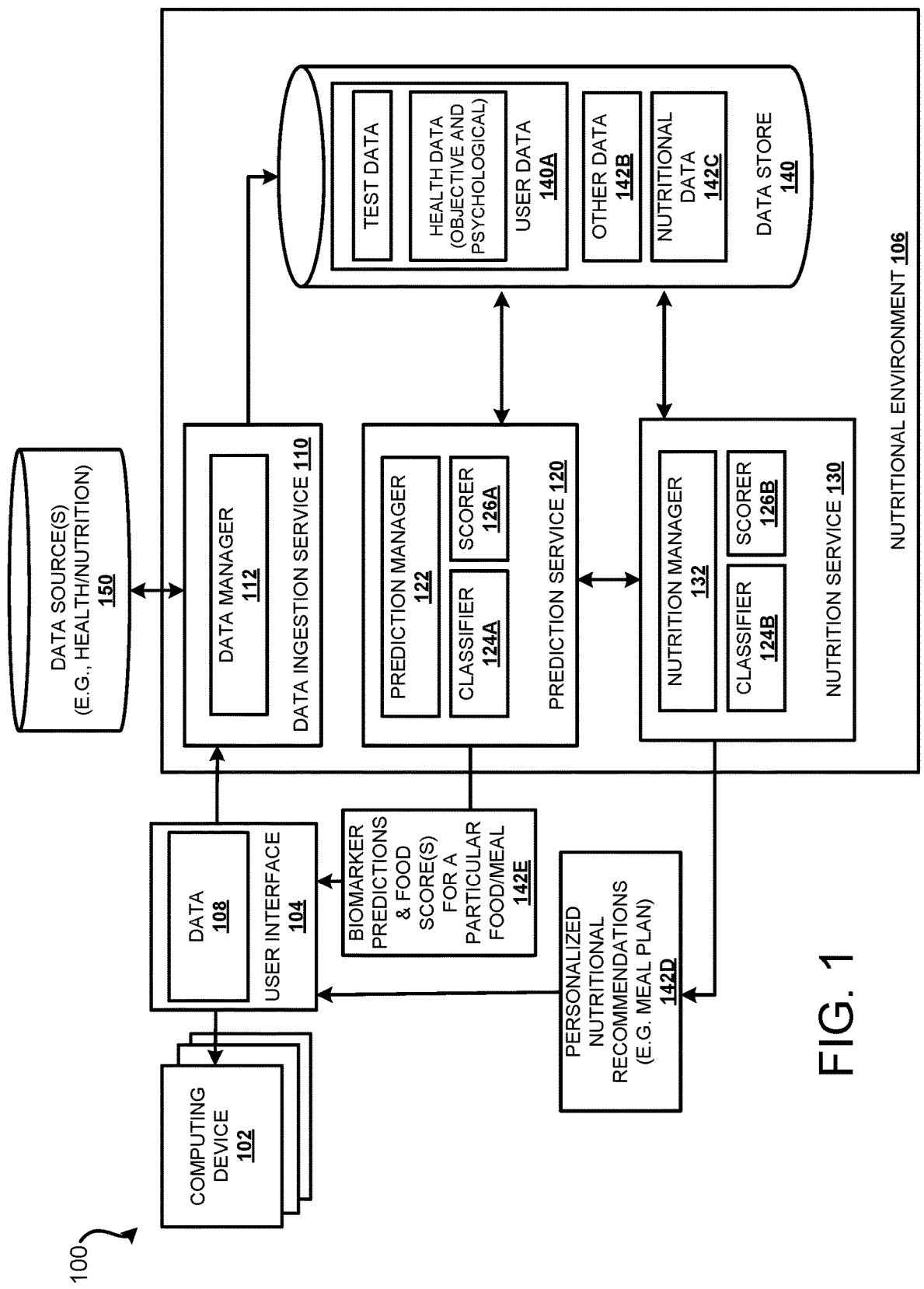
FIG. 1 is a block diagram depicting an illustrative operating environment in which personalized nutritional recommendations are generated using predicted values of target biomarkers.

The following detailed description is directed to technologies for generating personalized nutritional recommendations using predicted values of target biomarkers. Using the technologies described herein, a programmatic analysis is performed on different data, associated with an individual, to predict values of target biomarkers. Using these predicted target biomarkers, a nutrition service generates personalized nutritional recommendations for the individual.

A "biomarker" or biological marker generally refers to a measurable indicator of some biological state or condition associated with an individual. Stated another way, a biomarker may be anything that can be used as an indicator of particular disease state or some other physiological state of an organism. A biomarker can typically be measured accurately (either objectively or subjectively) and the measurement is reproducible (e.g., blood glucose, triglycerides, insulin, ketone body ratios, IL-6 inflammation markers, hunger, fullness, and the like). The different data utilized to generate the predicted values of the biomarkers and the generation of the personalized nutritional recommendations can include many different types of health data such as microbiome data, blood data, glucose data, ketone data, nutrition data, wearable data, genetic data, biometric data, questionnaire data, psychological data (e.g., hunger, sleep quality, mood, . . . ), objective health data (e.g., age, sex, height, weight, medical history, . . . ), as well as other types of data. Generally, "health data" can refer to any psychological, subjective and/or objective data that relates to and is associated with one or more individuals. The health data might be obtained through testing, self-reporting, and the like.

In some examples, the data includes wearable data obtained from technology worn and/or utilized by an individual. For instance, an individual may wear a fitness device, such as an activity-monitoring device, that monitors motion, heart rate, determines how much a user has slept, the number of calories burned, activities performed, blood pressure, body temperature, and the like. The individual may also wear a continuous glucose meter that monitors blood glucose levels often by measuring levels of glucose in interstitial fluid.

An individual may also provide data that may be utilized to predict the target values and/or changes to the target values and generate the nutritional recommendations using other devices such as blood glucose monitors, finger pricks which in some examples are used with dried blood spot cards, blood pressure monitors, and the like. An individual may also input data into one or more software applications (or provide the data some other way) that can be utilized. For example, a user may enter the food they had during a meal, how much they slept, how hungry they are, how they feel, what medication they take, and the like. As another example, an individual may input test data determined from one or more tests, such as urinalysis test strips, blood test strips, and the like. The test data may come from different sources, such as but not limited to from one or more of an individual, a lab, a doctor, an organization, and/or some other data source.

Still further, in some cases, the individual can provide biological samples to a lab for testing. According to some configurations, users can provide a sample for microbiome analysis. As an example, metagenomic testing can be performed using the sample to allow the DNA of a microbiome of an individual to be digitalized. Generally, a microbiome analysis includes determining the composition and function of a community of microorganisms in a particular location, such as within the gut of a user. An individual's microbiome appears to have a strong causal relationship to metabolism, weight and health, yet only ten to thirty percent of the microbiome is common across different individuals.

After accessing the different types of data from an individual, a prediction service identifies the predicted value of different target biomarkers as predicted after eating one or more foods. In some configurations, the prediction service is configured to generate the predicted values of different target biomarkers for foods that are included in a meal or generate predicted values of target biomarkers for a single food. Instead of generating a prediction of a value (or a change in the value of a biomarker) for a single biomarker, the prediction service generates predictions for values of more than one biomarker. As discussed briefly above, the prediction of the value or the change in the value can be for a biomarker determined objectively (e.g., through a test, measurement by a device, . . . ) or subjectively (e.g., through user input). According to some examples, the prediction service predicts the values for the biomarkers associated with insulin, glucose, ketone bodies, triglycerides, hunger, and the like, for an individual. By combining the predicted values of the biomarkers for a particular food or meal, the prediction service can generate a score for that food or meal.

The prediction service can utilize data received from an individual and data received from other individuals. For example, the prediction service can utilize training data obtained from a number of individuals (e.g., >100, 500, 1000, . . . ). This test group of individuals may be subject to similar tests and procedures thereby providing reliable data that can be utilized by the prediction service and/or the nutrition service. In some configurations, the training data is utilized to train one or more machine learning mechanisms that can be used by the prediction service and/or the nutrition service.

A nutrition service is configured to generate nutritional recommendations that are personalized for the user. The nutrition service communicates with the prediction service in generating the nutritional recommendations for the user. The nutrition service is configured to generate nutritional recommendations for some period of time (e.g., one meal, two meals, a week of meals, a month of meals, and the like). In some examples, the nutrition service utilizes the prediction service to generate predictions of values (or changes in values) for at least two biomarkers for different food choices. For instance, the nutrition service can instruct the prediction service to generate predictions for five, ten, twenty, thirty, or more combination of food choices for one or more meals. In some examples the nutrition service takes objectives (e.g., reduce weight, avoid high blood glucose levels, avoid cardiovascular disease, move the microbiome towards a target microbiome . . . ) and calculates target outcomes or ranges for two or more biomarkers. The nutrition service utilizes the predictions to generate the nutritional recommendations based on the objectives, preferences from the user (e.g., the user does not like certain foods or likes certain foods), as well as other data such as the daily meals should total X calories, contain X number servings of vegetables, have X amount of fiber content, and the like.

Using the technologies described herein, an individual is provided with accurate, personalized food choices. Instead of providing a diet with food choices aimed at the general population, the food choices are personalized for the individual. As such, an individual may be able to reduce weight, improve their metabolism and microbiome, avoid obesity and improve health outcomes including diseases such as cardiovascular disease, type 2 Diabetes, metabolic syndrome and the like more effectively as compared to following nutritional recommendations aimed at the general population.

Additional details regarding the various components and processes described above relating to generating personalized nutritional recommendations using predicted values of target biomarkers will be presented below with regard to FIGS. 1-7.

It should be appreciated that the subject matter presented herein may be implemented as a computer process, a computer-controlled apparatus, a computing system, or an article of manufacture, such as a computer-readable storage medium. While the subject matter described herein is presented in the general context of program modules that execute on one or more computing devices, those skilled in the art will recognize that other implementations may be performed in combination with other types of program modules. Generally, program modules include routines, programs, components, data structures and other types of structures that perform particular tasks or implement particular abstract data types.

Those skilled in the art will also appreciate that aspects of the subject matter described herein may be practiced on or in conjunction with other computer system configurations beyond those described herein, including multiprocessor systems, microprocessor-based or programmable consumer electronics, minicomputers, mainframe computers, handheld computers, personal digital assistants, e-readers, mobile telephone devices, tablet computing devices, special-purposed hardware devices, network appliances and the like.

In the following detailed description, references are made to the accompanying drawings that form a part hereof, and that show, by way of illustration, specific examples or examples. The drawings herein are not drawn to scale. Like numerals represent like elements throughout the several figures (which may be referred to herein as a "FIG." or "FIGS.").

FIG. 1 is a block diagram depicting an illustrative operating environment 100 in which personalized nutritional recommendations are generated using predicted values of target biomarkers. A user, such as an individual requesting personalized food recommendations, may communicate with the nutritional environment 106 using a computing device 102. In some configurations, the user is a customer of the nutritional environment 106.

As illustrated in FIG. 1, the operating environment 100 includes one or more computing devices 102 in communication with a nutritional environment 106. In some examples, the nutritional environment 106 may be associated with and/or implemented by resources provided by a service provider network such as provided by a cloud computing company. The nutritional environment 106 includes a data ingestion service 110, a prediction service 120, a nutrition service 130, and a data store 140.

The nutritional environment 106 may include a collection of computing resources (e.g., computing devices such as servers). The computing resources may include a number of computing, networking and storage devices in communication with one another. In some examples, the computing resources may correspond to physical computing devices and/or virtual computing devices implemented by one or more physical computing devices.

It should be appreciated that the nutritional environment 106 may be implemented using fewer or more components than are illustrated in FIG. 1. For example, all or a portion of the components illustrated in the nutritional environment 106 may be provided by a service provider network (not shown). In addition, the nutritional environment 106 could include various Web services and/or peer-to-peer network configurations. Thus, the depiction of the nutritional environment 106 in FIG. 1 should be taken as illustrative and not limiting to the present disclosure.

The data ingestion service 110 facilitates submission of data utilized by the prediction service 120 and nutrition service 130. Accordingly, utilizing a computing device 102, a user may submit data 108 to the nutritional environment 106 via the data ingestion service 110. The data may also be obtained by the data ingestion service 110 from other data sources, such as data source(s) 150. For example, the data source(s) 150 can include, but are not limited to nutritional data (e.g., nutrition of particular foods, nutrition associated with the individual, and the like), health data associated with the individual and/or other individuals, and the like.

The data, such as data 108, or the data obtained from one or more data sources 150, may then be processed by the data manager 112 and included in a data store, such as the data store 140. As illustrated, the data store 140 can be configured to store user data 140A, other data 142B, and nutritional data 142C (See FIG. 2 for more details on the data ingestion service 110). In some examples, the user data 140A includes test data and health data that can include psychological data, subjective data and objective health data. As briefly discussed above, one of the data sources 150 may be the training data that can be obtained from a number of individuals (e.g., >100, 500, 1000, . . . ). This group of individuals may be subject to similar tests and procedures thereby providing consistent, reliable data that can be utilized by the prediction service and/or the nutrition service.

As discussed in more detail below, the prediction service 120 utilizing the prediction manager 122 can predict target values for a plurality of different biomarkers for one or more foods, such as a meal (e.g., lasagna with broccoli) or a snack (e.g., a banana). As discussed briefly above, the prediction service 120 can be configured to generate a predicted value for each of the biomarkers and/or configured to generate a prediction on how much a value of each of the biomarkers will change based on the food(s) being analyzed. In some examples, the prediction may be for biomarkers determined objectively (e.g., through a test, measurement by a device, . . . ). In other examples, the prediction may be for biomarkers subjectively determined (e.g., through input from the individual). According to some examples, the prediction service 120 predicts the values for the biomarkers associated with insulin, glucose, ketone bodies, triglycerides, IL-6 inflammation, hunger, fullness, mood, and the like for an individual.

In some examples, the prediction manager 122 may utilize one or more machine learning mechanisms. For example, the prediction manager 122 can use a classifier 124A to classify the predicted value of a biomarker within a classification category. In other examples, the prediction manager 122 may use a scorer 126A to generate a score that provides an indication of how likely one or more foods is likely to affect one or more of the target biomarkers. In some configurations, the prediction manager 122 combines the different predictions to generate a single score for the food(s). In other configurations, the prediction manager 122 provides the individual predictions for each of the different biomarkers.

The prediction service 120 can generate one or more user interfaces, such as a user interface 104, through which a user, utilizing the computing device 102, or some other computing device, may provide/receive the information via the nutritional environment 106. For example, the prediction service 130 may provide the biomarker predictions 142E for a particular food/meal via the user interface 104.

As briefly mentioned above, instead of focusing on predicting a value of a single biomarker (e.g., a blood glucose response) to a meal, the prediction service 120 predicts values for many different biomarkers. In some examples, the prediction service 120 predicts the biochemical fingerprint of insulin, glucose, ketone bodies, IL-6 inflammation and triglycerides after a meal. Insulin, glucose and triglycerides are components that can affect body weight. An individual whose concentrations of these biomarkers spike regularly above the average level is likely to be predisposed to weight-gain, owing to an elevated systemic energy content (glucose and triglycerides) and the capacity to store these substrates (owing to the abundance of insulin).

A nutrition service 130 utilizes predicted values of the biomarkers generated by the prediction manager 122 of the prediction service 122, along with the user data 140A, other data 142B, and/or nutritional data 142C, to generate personalized nutritional recommendations for the individual. The nutrition service 130 is configured to provide an individual with personalized nutritional recommendations such as a meal plan. As such, an individual may be able to reduce weight, improve their metabolism and microbiome, avoid obesity and improve health outcomes including diseases such as cardiovascular disease, type 2 Diabetes, metabolic syndrome and the like more effectively as compared to following nutritional recommendations aimed at the general population.

In addition, to determining foods that are healthy for a particular individual, the nutrition service 130 can utilize the data to assist in moving biomarkers (e.g., the gut microbiome) toward a target. For example, the nutrition service 130 can be configured to identify foods that move the microbiome of an individual to a target microbiome "fingerprint". Targeting microbiome improvements for an individual can lead to an improvement of an individual's health responses to foods. As used herein, the term "fingerprint" refers to a mixture of bacteria in the gut microbiome that are associated with an individual.

The nutrition service 130 communicates with the prediction service 120 in generating the personalized nutrition recommendations 142D for the user. The nutrition service 130 may be configured to generate nutritional recommendations for more than one meal or food. For instance, the nutrition service 130 generates meals for a period of time (e.g., a single meal, a day, a week, a month, a year, . . . ).

The nutrition service 130 can take objectives (e.g., reduce weight, avoid high blood glucose levels, avoid cardiovascular disease, move the microbiome towards a target microbiome . . . ) and calculate target outcomes or ranges for two or more biomarkers. In some configurations, the nutrition service 130 can take objectives that specify specific target values and/or a range of values for one or more biomarkers.

In some examples, the nutrition service 130 utilizes the prediction service 120 to generate predictions of values (or changes in values) for at least two biomarkers for different food choices. For instance, the nutrition service 130 can instruct the prediction service 120 to generate predictions for five, ten, twenty, thirty, or more combination of food choices for one or more meals. The nutrition service 130 utilizes the predictions generated by the prediction service 120 to generate nutritional recommendations based on the objectives for the biomarkers, preferences from the user (e.g., the user does not like certain foods or likes certain foods), as well as other data such as the daily meals should total X calories, contain X number servings of vegetables, have X amount of fiber content, and the like.

The nutrition service 130 can generate one or more user interfaces, such as a user interface 104, through which a user, utilizing the computing device 102, or some other computing device, may provide/receive the information via the nutritional environment 106. For example, the nutrition service 130 may provide the personalized nutritional recommendations 142D via the user interface 104.

While the data ingestion service 110, the prediction service 120, and the nutrition service 130 include components illustrated within each of the services, all or a portion of these services may be located in other locations or together with other components. For example, the data ingestion service 110 may be located within the prediction service 120. Similarly, the prediction manager 122 may be part of a different service, and the like.

The prediction service 120 and the nutrition service 130 may utilize one or more mechanisms for predicting the values of target biomarkers and generating the personal nutritional recommendations. For example, and without limitation, the prediction manager 122 can utilize classifier 124A to classify the predicted score of each of the biomarkers into a classification category. For example, the predicted score for a biomarker may be classified into a classification category indicating that the predicted value is within a healthy range or a non-healthy range. Alternatively, the classification category may be predicted directly by the classifier 124A without using an intermediate predicted score. A logistic regression mechanism, random forests, gradient boosting, neural networks or some other type of mechanism may be used by the classifier 124A for direct prediction of a classification category. Similarly, the nutrition manager 132 can utilize classifier 124B to classify a food within a classification category (e.g., recommended/not-recommended).

In other examples, the scorer 126A and/or scorer 126B may utilize another type of mechanism. According to some configurations, the prediction service 120 may utilize a scorer 126A to generate a score (e.g., a numerical value) for the predicted value of each of the target biomarkers. A linear regression mechanism, random forests, gradient boosting, neural networks or some other type of mechanism, may be used by the scorer 126A to generate a score for the predicted value of the biomarker. Any such mechanism can also be utilized by the scorer 126B.

In some configurations, the parameters utilized by the classifier 124 and/or the scorer 126 may be adjusted by a machine learning mechanism. The term "machine learning" may refer to one or more programs that learns to model the relationship between variables from the training data it receives. For example, a machine learning mechanism may build, modify or otherwise utilize a model that is created from example inputs and makes predictions or decisions using the model. In the current example, a machine learning mechanism may be used to identify recommended foods for a particular user and/or predict the value of a biomarker. The model used by the machine learning mechanism may be trained using supervised and/or unsupervised learning. For instance, over time as the machine learning mechanism receives more data, the predicted values and/or the recommended foods that are identified may change based on actual data associated that is received. Different machine learning mechanisms may be utilized. For example, classification or regression approaches using mechanisms such as linear regression, logistic regression, random forests, gradient boosting, neural networks or some other type of mechanism may be utilized. Such machine learning mechanisms might adjust model parameters to improve a least squares fit, achieve a maximum-likelihood estimation, or following another approach.

Figure 2:
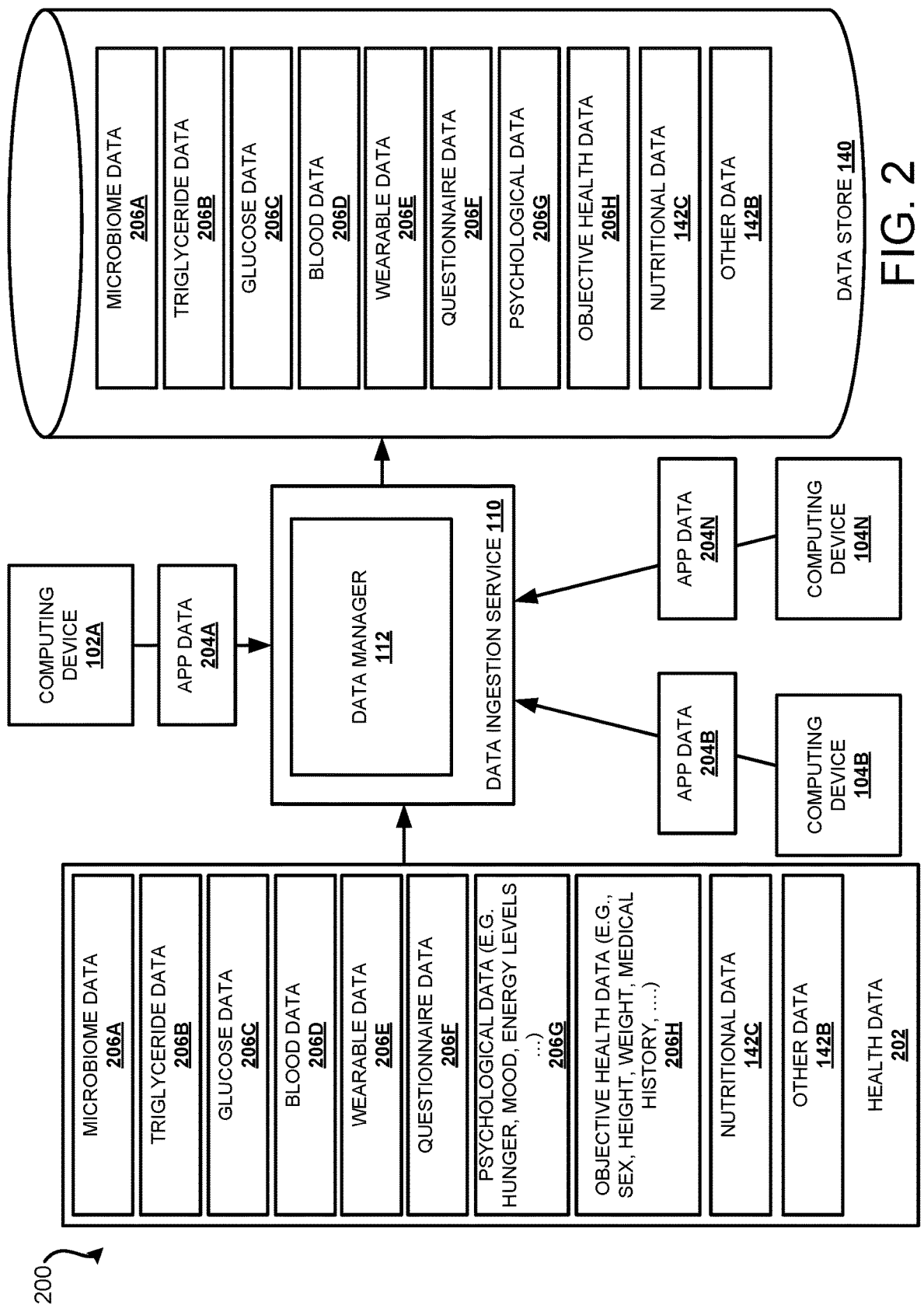
FIG. 2 is a block diagram depicting an illustrative operating environment in which a data ingestion service receives and processes data associated with generating personalized nutritional data.

FIG. 2 is a block diagram depicting an illustrative operating environment 200 in which a data ingestion service 110 receives and processes data associated with generating personalized nutritional recommendations. As illustrated in FIG. 2, the operating environment 200 includes the data ingestion service 110 that may be utilized in ingesting data utilized by the prediction service 120 and the nutrition service 130.

In some configurations, the data manager 112 is configured to receive data such as, health data 202 that can include, but is not limited to microbiome data 206A, triglyceride data 206B, glucose data 206C, blood data 206D, wearable data 206E, questionnaire data 206F, psychological data (e.g., hunger, sleep quality, mood, . . . ) 206G, objective health data (e.g., height, weight, medical history, . . . ) 206H, nutritional data 142C, and other data 142B. While not illustrated, other data may be received by the data manager 112.

According to some examples, the microbiome data 206A includes data about the gut microbiome of an individual. The gut microbiome can host a large number of bacterial species (e.g., >1000) that together have millions of genes. Imbalance of the normal gut microbiota have been linked with gastrointestinal conditions such as inflammatory bowel disease (IBD) and irritable bowel syndrome (IBS), and wider systemic manifestations of disease such as obesity, type 2 diabetes, and atopy. The bacteria of the gut undertake a variety of metabolic functions and are able to produce a variety of vitamins, synthesize essential and nonessential amino acids, and provide other functions. The microbiome of an individual provides biochemical pathways for the metabolism of nondigestible carbohydrates, which include large polysaccharides, such as resistant starches, cellulose, hemicellulose, pectins, and gums; some oligosaccharides that escape digestion; unabsorbed sugars and alcohols from the diet; and host-derived mucins.

The triglyceride data 206B may include data about triglycerides for an individual. In some examples, the triglyceride data 206B can be determined from a blood test and/or from a finger prick on to a dried blood spot card. The glucose data 206C includes data about blood glucose. The glucose data 206C may be determined from various testing mechanisms, such as a continuous glucose meter.

The blood data 206D may include blood tests relating to a variety of different biomarkers. In some configurations, the blood data 206D is associated with measuring blood sugar, insulin, triglycerides, IL-6 inflammation, ketone bodies, nutrient levels, allergy sensitivities, iron levels, blood count levels, HbA1c, and the like.

The wearable data 206E can include any data received from a computing device associated with a user. For instance, an individual may wear a fitness device, such as an activity-monitoring device, that monitors motion, heart rate, determines how much a user has slept, the number of calories burned, activities performed, blood pressure, body temperature, and the like. The individual may also wear a continuous glucose meter that monitors blood glucose levels.

The questionnaire data 206F can include data received from one or more questionnaires, and/or surveys received from one or more individuals. The psychological data 206G, that may be subjectively obtained, may include data received from the individual and/or a computing device that generates data or input based on a subjective determination (e.g., the individual states that they are still hungry after a meal, or a device estimates sleep quality based on a movement of the user at night). The objective health data 206H includes data that can be objectively measured, such as but not limited to height, weight, medical history, and the like.

The nutritional data 142C can include data about food. For example, the nutritional data can include nutritional information about different food(s) such as their macronutrients and micronutrients or the bioavailability of its nutrients under different conditions (raw vs cooked, or whole vs ground up). The other data 142B can include other data associated with the individual. For example, the other data 142B can include questionnaire data that can be received directly from a computer application that logs information for a user (e.g., food eaten, sleep, . . . ) and/or from the user via a user interface. In some examples, the other data 142B includes preferences, such as favorite foods, and disliked foods specified by an individual.

In some examples, different computing devices 102 associated with different users provide application data 204 to the data manager 112 for ingestion by the data ingestion service 110. As illustrated, computing device 102A provides app data 204A to the data manager 112, computing device 102B provides app data 204B to the data manager 112, and computing device 102N provides app data 204N to the data manager 112.

As discussed briefly above, the data manager 112 receives data from different data sources, processes the data when needed (e.g., cleans up the data for storage in a uniform manner), and stores the data within one or more data stores, such as the data store 140.

The data manager 112 can be configured to perform processing on the data before storing the data in the data store 140. For example, the data manager 112 may receive data for ketone bodies and then use that data to generate ketone body ratios. Similarly, the data manager 112 may process food eaten and generate meal calories, number of carbohydrates, fat to carbohydrate rations, how much fiber consumed during a time period, and the like.

Figure 3:
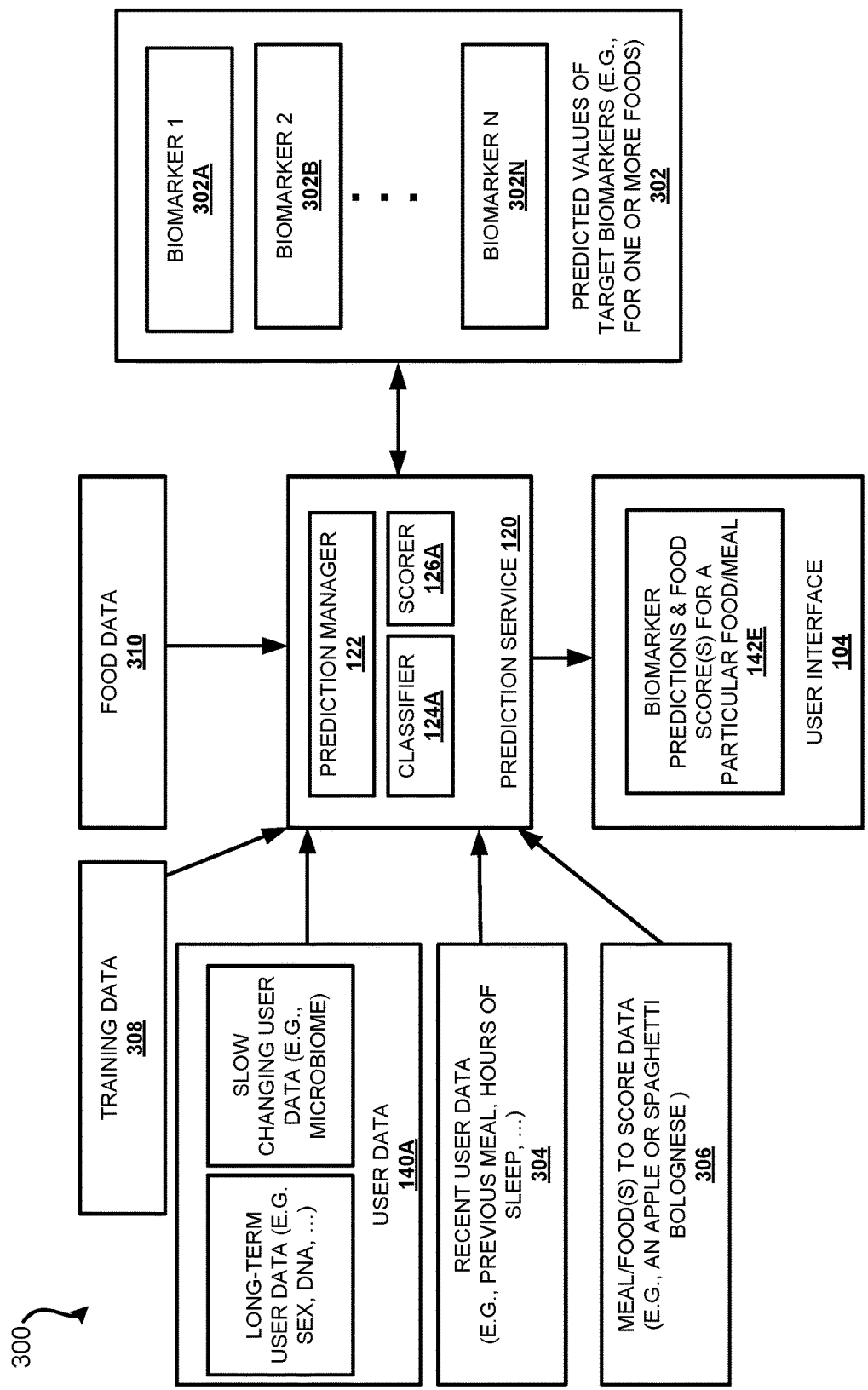
FIG. 3 is a block diagram depicting an illustrative operating environment in which a prediction service generates prediction of target biomarkers utilizing machine learning and user data.

FIG. 3 is a block diagram depicting an illustrative operating environment 300 in which a prediction service 120 generates prediction of target biomarkers (302A-302N) utilizing machine learning and data. As illustrated in FIG. 3, the operating environment 300 includes the prediction service 120 that includes prediction manager 122, classifier 124A and scorer 126A.

As illustrated, the prediction service 120, via the prediction manager 122, receives user data 140A, recent user data 304, food(s) to score data 306, training data 308, and food data 310. The prediction manager 122 utilizes the user data 140A, the recent user data 304, the meal/food(s) to score data 306, the training data 308, the food data 310 and possibly other data (not shown) to predict target values for biomarkers 302 for a particular meal or food. As illustrated, the prediction manager 122 generates values for biomarkers 1 (302A) through biomarker N (302N). As discussed above, the biomarkers may be measured through a test, a measuring device, and/or through subjective measurement. For example, biomarker 1 (302A) can be a biomarker associated with "glucose levels", whereas biomarker 2 (302B) can be a biomarker associated with how "hungry" a user feels either before or after a meal.

The user data 140A includes slow changing user data associated with a particular individual that is relatively slow changing (e.g., microbiome, weight, . . . ) and long-term user data that is static in nature, such as but not limited to sex, DNA, and the like. The recent user data 304 includes data that is recent in time (e.g., the same day), such as but not limited to recent food eaten by the individual (e.g., the previous meal of the individual), how much sleep the user has had, activity level, the mood of the individual, the hunger of the individual, and the like. The meal/food(s) to score data 306 includes data identifying the food(s) the prediction service 120 is to utilize when generating the predicted values (or changes in values).

The training data 308 includes data obtained from a group of individuals. In some examples, at least a portion of the training data 308 includes data obtained in a structured environment (e.g., a clinical study). For example, the training data 308 may include a large number of individual data points (e.g., >500 people, >1000 people, >10000 people). Generally, the more individual data points that are included within the training data 308, the more accurate the personalized nutritional recommendations may be. According to some configurations, the training data 308 may expand to include further individual data points. For example, as individuals add data, the training data 308 can be updated automatically and/or manually to include the data. The food data 310 can include data associated with the food(s) to score data 306, such as nutritional data.

As discussed, the prediction service 120 can utilize a machine learning mechanism. The machine learning mechanism can be trained to predict scores for different biomarkers for different food(s). According to some examples, the machine learning mechanism, or some other scoring mechanism weights the different data used to generate the predictions, such that data that is more accurate (e.g., test data received from individuals in a structured setting, such as a hospital setting, or a lab setting) is provided more weight as compared to data that is not as reliable (e.g., a test performed in an un-structured setting, such as at a home setting that is not as reliable as that done in a hospital setting).

In some examples, the prediction service 120 generates a predicted value for a target biomarker, such as biomarker 1 (302A) before moving onto predicting a value for a next biomarker, such as one of biomarker 2-biomarker N.

According to some examples, the prediction manager 122 utilizes the scorer 126A to generate a score (e.g., a numerical value) for the target biomarker. In other examples, the prediction manager 122 utilizes the classifier 124A to place the target biomarker into a category (e.g., very low, low, average, high, very high) or some other category (e.g., a category based on the value of the score). Generally, the value of a biomarker is dependent on the food of the current meal as included within the meal/food(s) to score data 306. For example, the meal/food(s) to score data 306 can include data indicating that the user ate a banana and spaghetti noodles. In some configurations, the biomarkers predicted are biomarkers that change within some predetermined amount of time from ingestion of the meal (e.g., within a few hours). In many cases, a biomarker can affect a slower moving biomarker, for example HbA1c is a slow moving biomarker affected over a few months by the fast moving biomarker blood glucose.

As briefly discussed above, the prediction service 120 can generate one or more user interfaces, such as a user interface 104, through which a user, utilizing the computing device 102, or some other computing device, may interact with the prediction service 120 and input or view data, such as the biomarker predictions & food score(s) 142E for a particular food/meal via the user interface 104.

Figure 4:
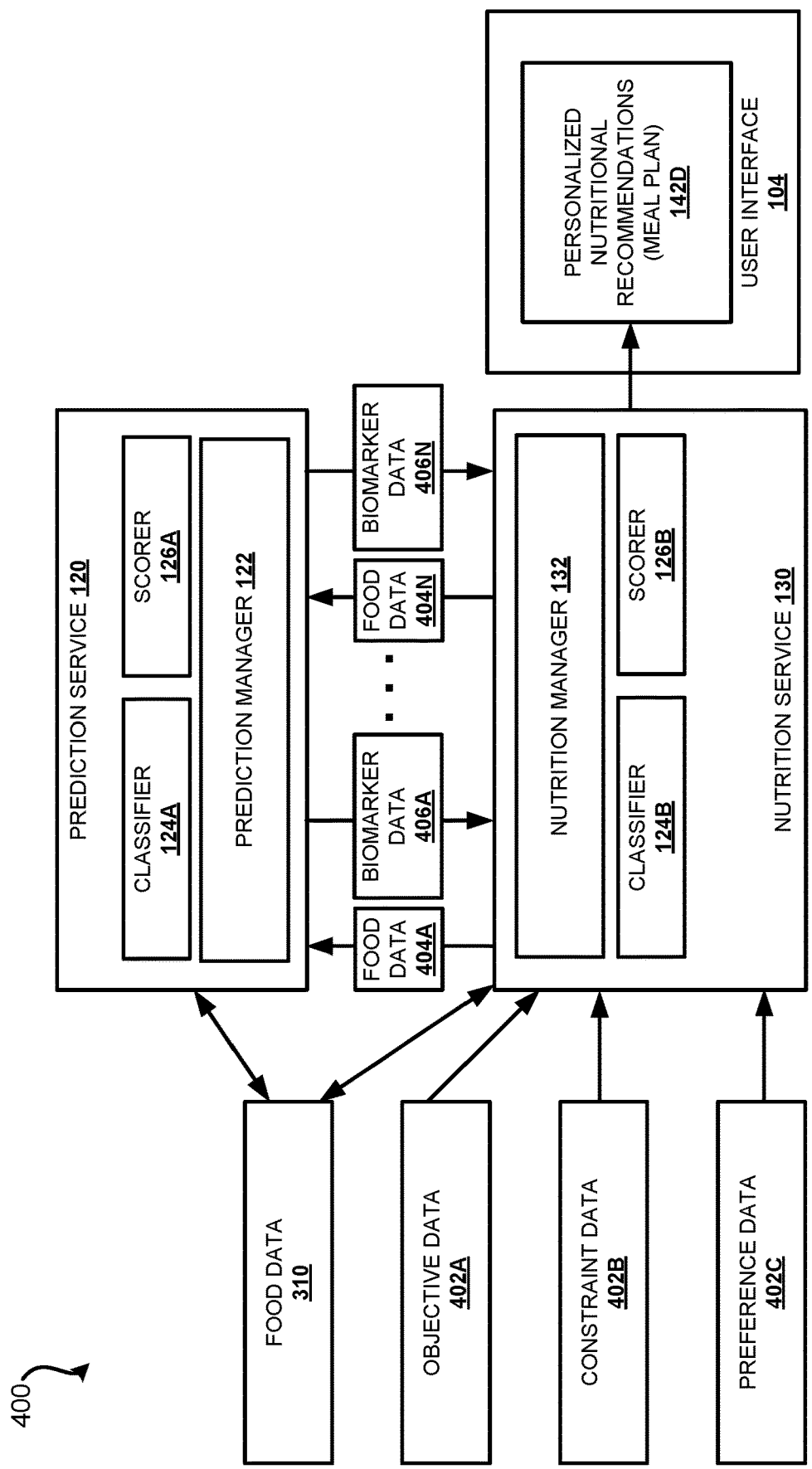
FIG. 4 is a block diagram depicting an illustrative operating environment in which a nutrition service generates personalized nutritional recommendations utilizing predicted values of target biomarkers.

FIG. 4 is a block diagram depicting an illustrative operating environment 400 in which a nutrition service 130 generates personalized nutritional recommendations utilizing predicted values of target biomarkers. As illustrated in FIG. 4, the operating environment 400 includes the prediction service 120, and the nutrition service 130 that includes nutrition manager 132, classifier 124B and scorer 126B.

The nutrition service 130 is configured to receive objective data 402A, constraint data 402B, preference data 402C, and food data 310. The nutrition service 130 also receives predicted values of target biomarker data (406A-406N) from the prediction service 120. As discussed above, the nutrition manager 132 uses the prediction service 120 to generate predicted values of target biomarkers for different foods when generating the personalized nutritional recommendations 142D for a particular user. The nutrition manager 132 can determine how a variety of different foods meet the objectives, constraints, and preferences when generating the personalized nutritional recommendations 142D.

The objective data 402A includes one or more objectives for the nutritional recommendations for an individual. For example, one objective may be to increase the health of the individual, another objective may be to decrease the weight of an individual, another objective may be to limit glucose to below a specified value, another objective may be to target triglycerides to a specific value, and the like. Other objectives may be to improve sleep quality, whereas yet another objective may be to decrease cholesterol. In some configurations, where the objective is not for a target value or target range for one or more biomarkers, the nutrition manager 132 can map the objective to a target value or target range for one or more biomarkers (for example a cardiovascular health objective may be mapped to targeting the biomarker triglyceride to remain below a certain level).

The constraint data 402B indicates the constraints that are associated with the nutritional recommendations of the individual. For example, constraints may include limits, or ranges for different nutritional aspects (e.g., carbohydrates, fat, protein, . . . ), restrictions on type of foods (e.g., a specified number of servings of vegetables per day), how many calories to eat, requirements for variety in meals, and the like.

The preference data 402C indicates the preferences of the user. For example, an individual may provide a list of favorite foods, types of foods, and the like. In this way, the nutrition manager 132 can balance the likes/dislikes of the individual with the objectives for the nutritional recommendations 142D.

As discussed above, the nutrition service 130 utilizes the predicted values of the target biomarkers data 406A generated by the prediction manager 122 of the prediction service 120, along with other data such as the objective data 402A, the constraint data 402B, the preference data 402C and/or other data discussed herein, to generate personalized nutritional data recommendations 142D for the individual. As discussed above, the nutrition service 130 can provide the personalized nutritional recommendations 142D via the user interface 104 that can be presented on a display associated with a computing device, such as computing device 102.

The nutrition service 130 is configured to provide an individual with personalized food choices. As such, an individual may be able to reduce weight, improve their metabolism and microbiome, avoid obesity and improve health outcomes including diseases such as cardiovascular disease, type 2 Diabetes, metabolic syndrome and the like more effectively as compared to following nutritional recommendations aimed at the general population.

In addition, to determining foods that are healthy for a particular individual, the nutrition service 130 can utilize the data to assist in moving slow moving biomarkers (e.g., the gut microbiome) toward a target. For example, the nutrition service 130 can be configured to identify foods that move the microbiome of an individual towards a target microbiome "fingerprint". Targeting microbiome improvements for an individual can lead to an improvement of an individual's health responses to foods. As used herein, the term "fingerprint" refers to a mixture of bacteria in the gut that are associated with an individual.

As discussed above, the nutrition service 130 communicates with the prediction service 120 in generating the personalized nutritional recommendations 142D for the individual. As illustrated, the nutrition service 130 utilizes the prediction service 120 to generate predictions of values (or changes in values) for at least two biomarkers for different food choices. For instance, the nutrition service 130 can provide food data 404A to the prediction service 120 to generate predictions for at least two different biomarkers for a first food (or meal) and receive biomarker data 406A that provides the generated predictions for the first food. The nutrition service 130 can instruct the prediction service 120 to generate many different combinations of foods when determining the personalized nutritional recommendations. In the current example, the nutrition service 130 has requested N different predictions for N different foods. The nutrition manager 132 may generate nutritional recommendations for a single meal, a days' worth of meals, a weeks' worth of meals, a months' worth of meals, and the like. Generally, the nutrition manager 132 selects foods for particular meals such that the objectives, constraints, and preferences of the user are accounted for when developing the nutritional recommendations 142D.

The nutrition service 130 utilizes a mechanism, such as a machine learning mechanism to generate a selection of the foods to present within the personalized nutritional recommendations 142D. In some examples, the nutrition manager 132 utilizes the classifier 124B and/or the scorer 126B to rank the different food combinations. According to some configurations, the machine learning mechanism utilizes the biomarker data 406 along with the objective data, constraint data, and preference data as inputs to the machine learning mechanism. Stated another way, the nutrition manager 132 utilized the machine learning mechanism to generate nutritional recommendations 142D based on the objectives of the meals relative to the biomarkers (e.g., keep glucose triglycerides and insulin within these specified ranges, move the microbiome to a target microbiome . . . ), preferences from the user (e.g., the user does not like certain foods or likes certain foods), as well as other data such as the daily meals should total X calories, contain X number servings of vegetables, have X amount of fiber content, and the like.

Figure 5:
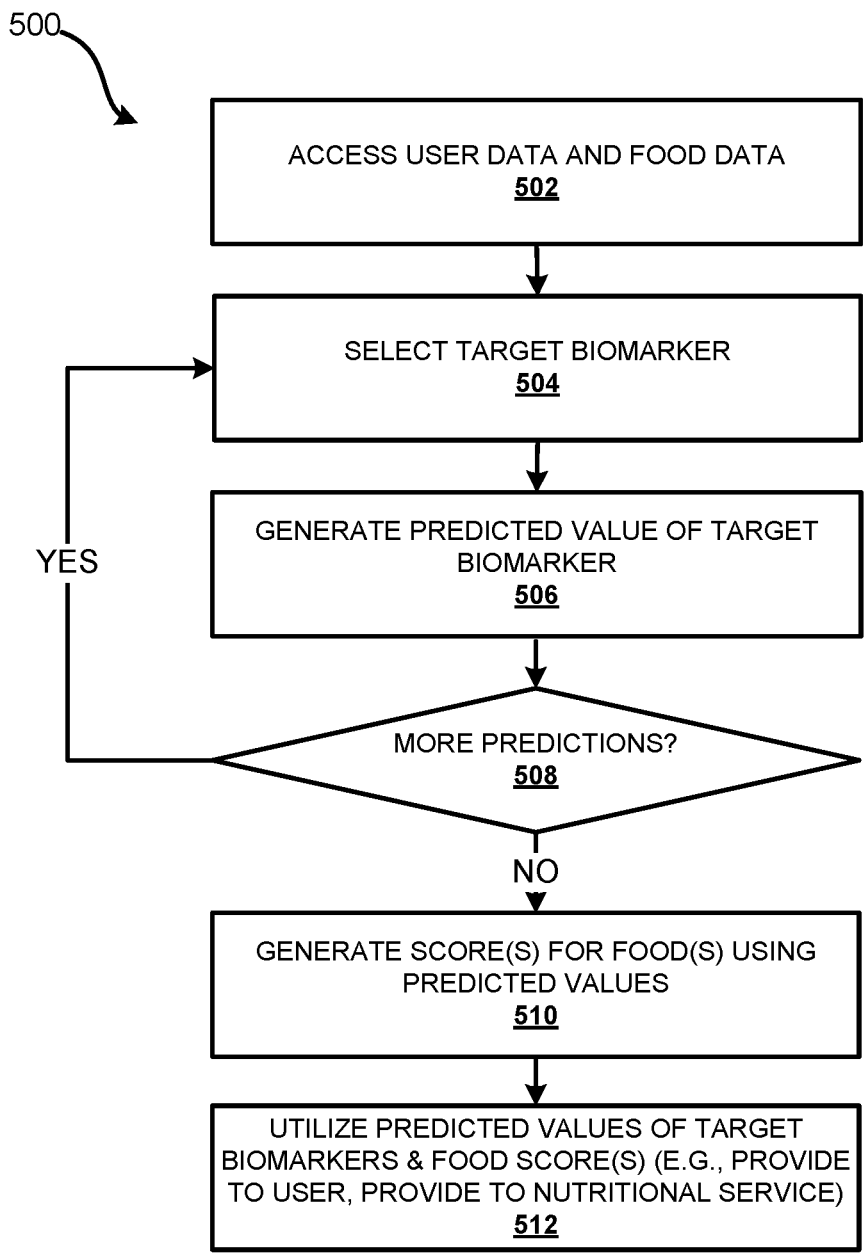
FIG. 5 is a flow diagram showing a routine illustrating aspects of a mechanism disclosed herein for predicting values of target biomarkers.
Figure 6:
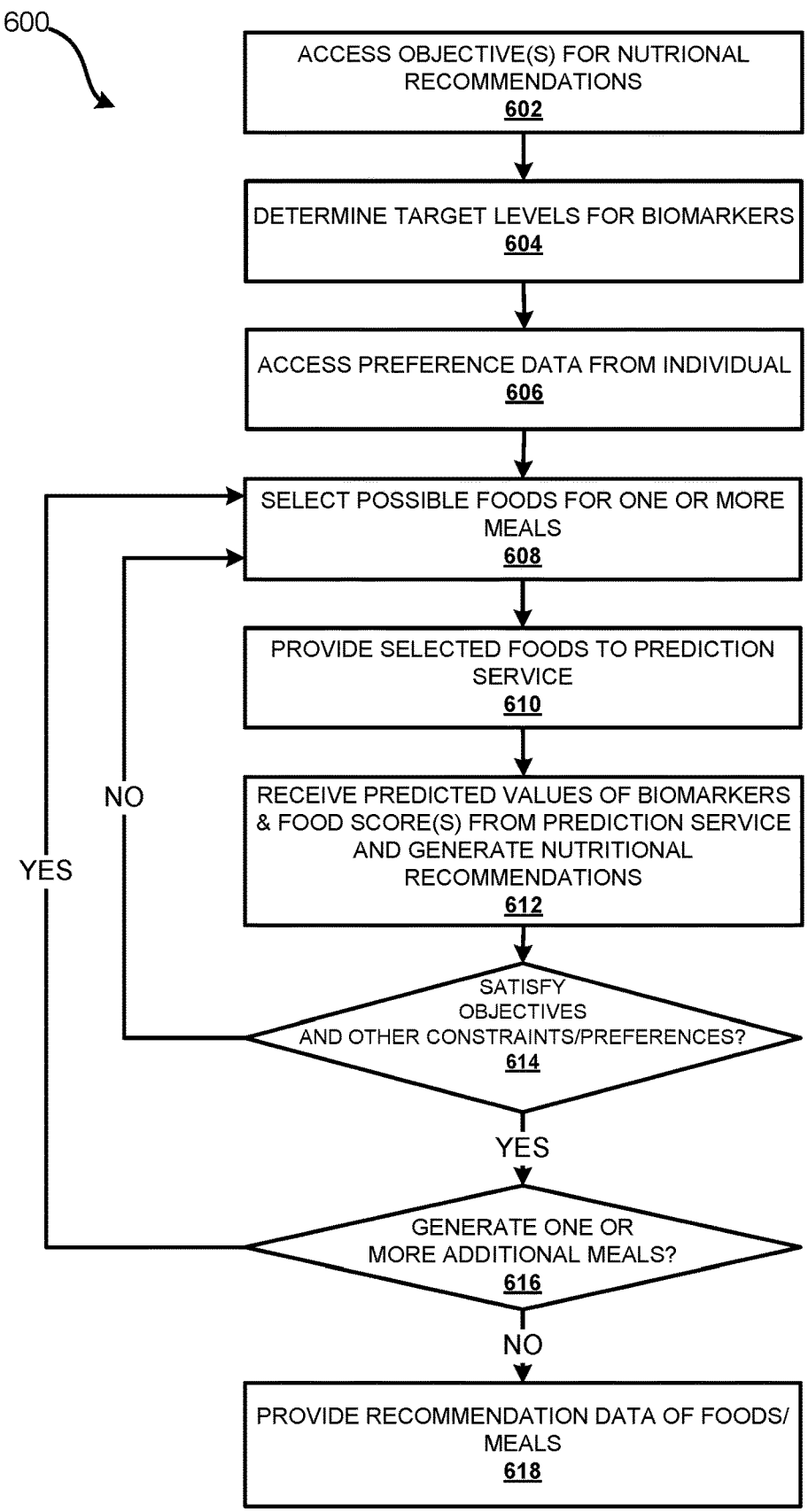
FIG. 6 is a flow diagram showing a routine illustrating aspects of a mechanism disclosed herein for generating personalized nutritional recommendations.

FIGS. 5 and 6 are flow diagrams showing routines 500 and 600, respectively that illustrate aspects of generating personalized nutritional recommendations using predicted values of biomarkers in accordance with examples described herein. It should be appreciated that the logical operations described herein with respect to FIGS. 5 and 6, and the other FIGS., may be implemented (1) as a sequence of computer implemented acts or program modules running on a computing system and/or (2) as interconnected machine logic circuits or circuit modules within the computing system.

The implementation of the various components described herein is a matter of choice dependent on the performance and other requirements of the computing system. Accordingly, the logical operations described herein are referred to variously as operations, structural devices, acts, or modules. These operations, structural devices, acts, and modules may be implemented in software, in firmware, in special purpose digital logic and any combination thereof. It should also be appreciated that more or fewer operations may be performed than shown in the FIGS. and described herein. These operations may also be performed in parallel, or in a different order than those described herein.

FIG. 5 is a flow diagram showing a routine 500 illustrating aspects of a mechanism disclosed herein for predicting values of target biomarkers. The routine 500 may begin at 502, where user data and food data is accessed and processed. As discussed above, different data is received by the data ingestion service 110, or some other computing device that is associated with the nutritional environment 106. In some examples, the prediction service 120 utilizes user data and food data for generating predictions associated with different biomarkers.

At 504, a target biomarker is selected for prediction. As discussed above, the target biomarker may be one of a number of different biomarkers. Instead of predicting a value of a single glucose biomarker, the prediction service 120 generates a prediction for at least two target biomarkers.

At 506, the prediction service 120 generates a predicted value (or change in value) of the currently selected target biomarker predicted after eating a particular food, or foods of a meal. As discussed above, the prediction manager 122 of the prediction service 120 can utilize a machine learning mechanism to generate the predictions.

At 508, a determination is made as to whether there are more predictions. When there are more predictions, the process returns to 504. Where there are no further predictions, the process moves to 510.

At 510, the predicted values of the target biomarkers are used to generate score(s) for the current food. According to some configurations, the prediction service 120 and/or the nutrition service 130 can generate a single score for an entire meal.

At 512, the generated score(s) and/or the predicted values of the target biomarkers are utilized. In some example, the nutrition service 130, via the nutrition manager 132 generates a list of meals and/or foods that are recommended for the user based at least in part on predictions for different foods. In other examples, the predictions and/or score(s) of the food are provided to the user, such as through a user interface 104.

FIG. 6 is a flow diagram showing a routine 600 illustrating aspects of a mechanism disclosed herein for generating personalized nutritional recommendations. The routine 600 may begin at 602, where the objective(s) for the nutritional recommendations(s) is set. As discussed above, the objectives can be preset by an authorized user and/or input using an input mechanism, such as a graphical user interface. In some examples, the objectives for the nutritional recommendations are set based on data associated with the user. For example, for an individual that desires blood glucose to stay below a target level, one of the objectives may be to limit a blood glucose response to a predefined level. The objectives can also include other objectives, such as but not limited to weight loss, gut microbiome targeting, triglycerides, and the like.

At 604, target levels for biomarkers are determined. As discussed above, in some examples, the objective may specify a target value or a range of target values for specific biomarkers. In other examples, the objective may specify a goal such as improve cardiovascular health, reduce weight, and the like. In these examples where the objective is not for a target value or target range for one or more biomarkers, the routine can map the objective to a target value or target range for one or more biomarkers (for example a cardiovascular health objective may be mapped to targeting the biomarker triglyceride to remain below a certain level).

At 606, preference data for an individual is accessed. As discussed above, the preference data can indicate the preferences of the individual and/or some other authorized individual. For example, the preference data can indicate favorite foods of the individual, foods the individual does not like, and the like.

At 608, possible foods for one or more meals are selected. As discussed above, the nutrition service 130 can select a number of different foods and combine those foods in different ways when generating one or more meal recommendations.

At 610, the nutrition service 130 provides the selected foods for each of the meals. As discussed above, the prediction service 120 generates predicted values of the selected target biomarkers in response to receiving the selected foods from the nutrition service 130 and/or from some other source (e.g., a user interface).

At 612, the predicted values of the biomarkers and/or food score(s) are received from the prediction service 120. As discussed above, the nutrition service 130 generates nutritional recommendations using the predicted values of the biomarkers and/or food score(s) along with the other data, such as the objective data, constraint data, and preference data associated with the individual.

At 614, a determination is made as to whether the one or more meals satisfy the objectives, constraints, and/or preferences. When not satisfied, the process returns to 606. When satisfied, the process moves to 614.

At 616, a determination is made as to whether one or more additional meals are to be generated. When more meals are to be generated, the process returns to 606. When more meals are not to be generated, the process moves to 616.

At 618, the recommendation data of the foods/meals is provided. In some examples, the recommendation data is provided via a user interface 104 that is displayed on a display associated with the computing device 102. In other configurations, the recommendation data can be included in an email, or some other electronic communication that is delivered to the user.

Figure 7:
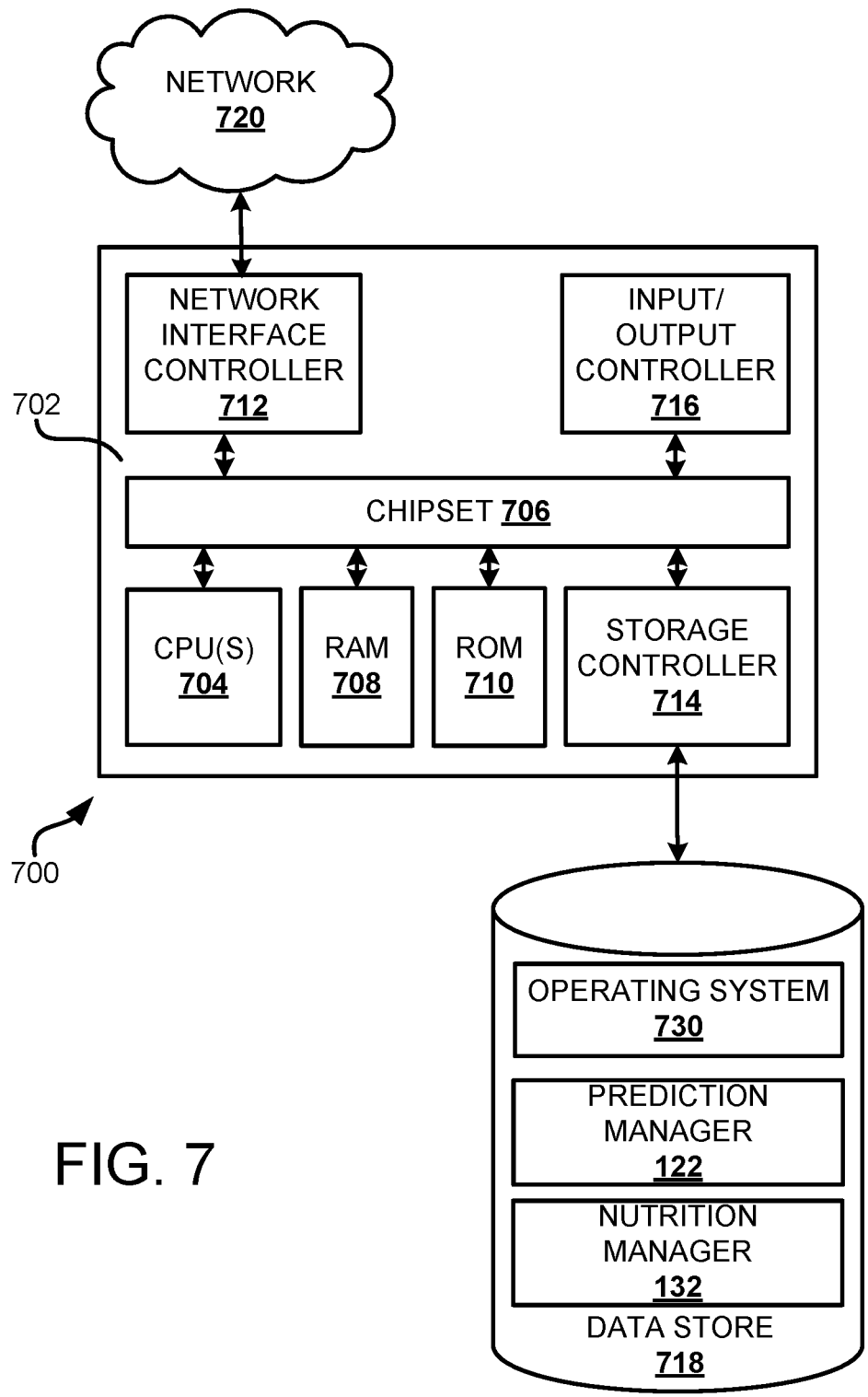
FIG. 7 is a computer architecture diagram showing one illustrative computer hardware architecture for implementing a computing device that might be utilized to implement aspects of the various examples presented herein.

FIG. 7 shows an example computer architecture for a computer 700 capable of executing program components for generating personalized nutritional recommendations using predicted values of target biomarkers in the manner described above. The computer architecture shown in FIG. 7 illustrates a conventional server computer, workstation, desktop computer, laptop, tablet, network appliance, digital cellular phone, or other computing device, and may be utilized to execute any of the software components presented herein. For example, the computer architecture shown in FIG. 7 may be utilized to execute software components for performing operations as described above. The computer architecture shown in FIG. 7 might also be utilized to implement a computing device 102, or any other of the computing systems described herein.

The computer 700 includes a baseboard 702, or "motherboard," which is a printed circuit board to which a multitude of components or devices may be connected by way of a system bus or other electrical communication paths. In one illustrative example, one or more central processing units ("CPUs") 704 operate in conjunction with a chipset 706. The CPUs 704 may be standard programmable processors that perform arithmetic and logical operations necessary for the operation of the computer 700.

The CPUs 704 perform operations by transitioning from one discrete, physical state to the next through the manipulation of switching elements that differentiate between and change these states. Switching elements may generally include electronic circuits that maintain one of two binary states, such as flip-flops and electronic circuits that provide an output state based on the logical combination of the states of one or more other switching elements, such as logic gates. These basic switching elements may be combined to create more complex logic circuits, including registers, adders-subtractors, arithmetic logic units, floating-point units and the like.

The chipset 706 provides an interface between the CPUs 704 and the remainder of the components and devices on the baseboard 702. The chipset 706 may provide an interface to a RAM 708, used as the main memory in the computer 700. The chipset 706 may further provide an interface to a computer-readable storage medium such as a read-only memory ("ROM") 710 or non-volatile RAM ("NVRAM")

for storing basic routines that help to startup the computer 700 and to transfer information between the various components and devices. The ROM 710 or NVRAM may also store other software components necessary for the operation of the computer 700 in accordance with the examples described herein.

The computer 700 may operate in a networked environment using logical connections to remote computing devices and computer systems through a network, such as the network 720. The chipset 706 may include functionality for providing network connectivity through a network interface controller ("NIC") 712, such as a mobile cellular network adapter or gigabit Ethernet adapter. The NIC 712 is capable of connecting the computer 700 to other computing devices over the network 720. It should be appreciated that multiple NICs 712 may be present in the computer 700, connecting the computer to other types of networks and remote computer systems.

The computer 700 may be connected to a mass storage device 718 that provides non-volatile storage for the computer. The mass storage device 718 may store system programs, application programs, other program modules and data, which have been described in greater detail herein. The mass storage device 718 may be connected to the computer 700 through a storage controller 714 connected to the chipset 706. The mass storage device 718 may consist of one or more physical storage units. The storage controller 714 may interface with the physical storage units through a serial attached SCSI ("SAS") interface, a serial advanced technology attachment ("SATA") interface, a fiber channel ("FC") interface, or other type of interface for physically connecting and transferring data between computers and physical storage units.

The computer 700 may store data on the mass storage device 718 by transforming the physical state of the physical storage units to reflect the information being stored. The specific transformation of physical state may depend on various factors, in different implementations of this description. Examples of such factors may include, but are not limited to, the technology used to implement the physical storage units, whether the mass storage device 718 is characterized as primary or secondary storage and the like.

For example, the computer 700 may store information to the mass storage device 718 by issuing instructions through the storage controller 714 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computer 700 may further read information from the mass storage device 718 by detecting the physical states or characteristics of one or more particular locations within the physical storage units.

In addition to the mass storage device 718 described above, the computer 700 may have access to other computer-readable storage media to store and retrieve information, such as program modules, data structures, or other data. It should be appreciated by those skilled in the art that computer-readable storage media is any available media that provides for the non-transitory storage of data and that may be accessed by the computer 700.

By way of example, and not limitation, computer-readable storage media may include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

The mass storage device 718 may store an operating system 730 utilized to control the operation of the computer 700. According to one example, the operating system comprises the LINUX operating system. According to another example, the operating system comprises the WINDOWS® SERVER operating system from MICROSOFT Corporation. According to another example, the operating system comprises the iOS operating system from Apple. According to another example, the operating system comprises the Android operating system from Google or its ecosystem partners. According to further examples, the operating system may comprise the UNIX operating system. It should be appreciated that other operating systems may also be utilized. The mass storage device 718 may store other system or application programs and data utilized by the computer 700, such as components that include the prediction manager 122, the nutrition manager 132 and/or any of the other software components and data described above. The mass storage device 718 might also store other programs and data not specifically identified herein.

In one example, the mass storage device 718 or other computer-readable storage media is encoded with computer-executable instructions that, when loaded into the computer 700, create a special-purpose computer capable of implementing the examples described herein. These computer-executable instructions transform the computer 700 by specifying how the CPUs 704 transition between states, as described above. According to one example, the computer 700 has access to computer-readable storage media storing computer-executable instructions which, when executed by the computer 700, perform the various routines described above with regard to FIGS. 3-4. The computer 700 might also include computer-readable storage media for performing any of the other computer-implemented operations described herein.

The computer 700 may also include one or more input/output controllers 716 for receiving and processing input from a number of input devices, such as a keyboard, a mouse, a touchpad, a touch screen, an electronic stylus, or other type of input device. Similarly, the input/output controller 716 may provide output to a display, such as a computer monitor, a flat-panel display, a digital projector, a printer, a plotter, or other type of output device. It will be appreciated that the computer 700 may not include all of the components shown in FIG. 7, may include other components that are not explicitly shown in FIG. 7, or may utilize an architecture completely different than that shown in FIG. 7.

Based on the foregoing, it should be appreciated that technologies for generating personalized nutritional recommendations using predicted values of target biomarkers have been presented herein. Moreover, although the subject matter presented herein has been described in language specific to computer structural features, methodological acts and computer readable media, it is to be understood that the invention defined in the appended claims is not necessarily limited to the specific features, acts, or media described herein. Rather, the specific features, acts and media are disclosed as example forms of implementing the claims.

The subject matter described above is provided by way of illustration only and should not be construed as limiting. Furthermore, the claimed subject matter is not limited to implementations that solve any or all disadvantages noted in any part of this disclosure. Various modifications and changes may be made to the subject matter described herein without following the example examples and applications illustrated and described, and without departing from the true spirit and scope of the present invention, which is set forth in the following claims.

What is claimed is:

1. A non-transitory computer-readable storage medium having computer-executable instructions stored thereupon which, when executed by a computer, cause the computer to:
   generate, by the computer or one or more computing devices, a weighting of one or more parameters used by a machine learning mechanism to be used to make improved personalized nutritional recommendation data for an individual based, at least in part, on health data that is associated with individuals and accessed from a data store, wherein the health data indicates relationships between different foods eaten by at least a portion of the individuals and measured biomarker responses for the at least the portion of the individuals;
   cause the machine learning mechanism, that uses the weighting, to execute, wherein executing the machine learning mechanism includes performing actions to:
      generate, via the machine learning mechanism, first prediction data indicating a first value of a first target biomarker predicted after eating one or more foods, wherein the first prediction data is based at least in part on the health data, wherein the first target biomarker is a first indicator associated with at least one of a particular disease state or some other physiological state of an organism;
      generate, via the machine learning mechanism, second prediction data indicating a second value of a second target biomarker predicted after eating the one or more foods, wherein the second target biomarker is a second indicator associated with at least one of a different particular disease state or some other different physiological state of an organism;
   cause the personalized nutritional recommendation data to be generated based at least in part on the generated first prediction data, the generated second prediction data, and one or more objectives associated with one or more of the first target biomarker and the second target biomarker, wherein the personalized nutritional recommendation data indicates one or more meals for the individual to eat that are directed at achieving the one or more objectives;
   generate an interface that when presented includes at least a portion of the personalized nutrition recommendation data; and
   cause the interface, that includes the at least a portion of the personalized nutrition recommendation data, to be displayed on a computing device associated with the individual for presentation.

2. The non-transitory computer-readable storage medium of claim 1, wherein causing the personalized nutritional recommendation data to be generated comprises determining that the one or more meals satisfy the one or more objectives and one or more constraints, wherein the constraints identify one or more of a calorie constraint, a type of food constraint, a food variety constraint, or a favorite type of food constraint.

3. The non-transitory computer-readable storage medium of claim 2, wherein the one or more objectives include a first objective to move a first value of the first target biomarker to at least one of a first target value or a first target range and/or to move a second value of the second target biomarker to at least one of a second target value or a second target range.

4. The non-transitory computer-readable storage medium of claim 1, wherein the health data includes one or more of microbiome data, long-term user data, or slow changing user data.

5. The non-transitory computer-readable storage medium of claim 1, wherein causing the personalized nutritional recommendation data to be generated includes causing prediction data for one or more foods indicated to be preferred by the individual to be generated by the machine learning mechanism.

6. The non-transitory computer-readable storage medium of claim 1, wherein causing the personalized nutritional recommendation data includes causing prediction data to be generated by the prediction mechanism for a plurality of foods associated with a plurality of meals.

7. The non-transitory computer-readable storage medium of claim 1, wherein the machine learning mechanism is based at least in part on training data that includes first health data obtained in a structured setting and second health data obtained in a non-structured setting.

8. The non-transitory computer-readable storage medium of claim 1, wherein the computer-executable instructions further cause the computer to rank foods indicated within the personal nutritional recommendation data and wherein causing the interface, that includes the at least the portion of the personalized nutritional recommendation data, comprises causing a graphical user interface to be generated that includes a list of the ranked foods.

9. A system, comprising:
   one or more processors, configured to
   generate, by way of the one or more processors, a weighting of one or more parameters used by a machine learning mechanism to be used to make improved personalized nutritional recommendation data for an individual based, at least in part, on health data that is associated with individuals and accessed from a data store, wherein the health data indicates relationships between different foods eaten by at least a portion of the individuals and measured biomarker responses for the at least the portion of the individuals;
   cause the machine learning mechanism, that uses the weighting, to execute, wherein executing the machine learning mechanism includes performing actions to:
      generate, via the machine learning mechanism, first prediction data indicating a first value of a first target biomarker predicted after eating one or more foods, wherein the first prediction data is based at least in part on health data associated with the individual;
      generate, via the machine learning mechanism, second prediction data indicating a second value of a second target biomarker predicted after eating the one or more foods, wherein the second prediction data is based at least in part on the health data associated with the individual;
   cause, via the one or more processors, the personalized nutritional recommendation data to be generated based at least in part on the generated first prediction data, the generated second prediction data, and one or more objectives associated with one or more of the first target biomarker and the second target biomarker, wherein the personalized nutritional recommendation data indicates one or more meals for the individual to eat that are directed at achieving the one or more objectives; and cause at least a portion of the personalized nutritional recommendation data to be displayed on a computing device associated with the individual.

10. The system of claim 9, wherein the health data includes one or more of microbiome data, long-term user data, or slow changing user data.

11. The system of claim 9, wherein causing the personalized nutritional recommendation data to be generated comprises determining that the one or more meals satisfy one or more constraints, wherein the constraints indicate one or more of a calorie constraint, a type of food constraint, or a favorite type of food constraint.

12. The system of claim 11, wherein the one or more objectives include a first objective to move a first value of the first target biomarker to a first target value and/or move a second value of the second target biomarker to a second target value.

13. The system of claim 9, wherein causing the personalized nutritional recommendation data to be generated includes causing prediction data for one or more foods indicated to be preferred by the individual to be generated by the machine learning mechanism.

14. The system of claim 9, wherein causing the personalized nutritional recommendation data to be generated includes causing predication data to be generated by the machine learning mechanism for a plurality of foods associated with a plurality of meals.

15. The system of claim 9, wherein the health data includes first health data obtained in a structured setting and second health data obtained in a non-structured setting.

16. The system of claim 9, wherein the one or more processors are further configured to rank foods indicated within the personal nutritional recommendation data and wherein causing the at least the portion of the personalized nutritional recommendation data to be displayed comprises causing a graphical user interface to be generated that includes a list of the ranked foods.

17. A method, comprising:

generating, by way of one or more computers, a weighting of one or more parameters used by a machine learning mechanism to make improved personalized nutritional recommendation data for an individual based, at least in part on, health data that is associated with a plurality of individuals and accessed from a data store, wherein the health data indicates relationships between different foods eaten by at least a portion of the individuals and measured biomarker responses for the at least the portion of the individuals;

causing the machine learning mechanism, that uses the weighting, to execute on the one or more computers, wherein executing the machine learning mechanism includes performing actions to:

generate, via the machine learning mechanism, first prediction data indicating a first value of a first target biomarker predicted after eating one or more foods, wherein the first prediction data is based at least in part on health data associated with the individual;

generate, via the machine learning mechanism, second prediction data indicating a second value of a second target biomarker predicted after eating the one or more foods, wherein the second prediction data is based at least in part on the health data associated with the individual;

causing the personalized nutritional recommendation data to be generated based at least in part on the generated first prediction data, the generated second prediction data, and one or more objectives associated with one or more of the first target biomarker and the second target biomarker, personalized nutritional recommendation data that indicates one or more meals for the individual to eat that are directed at achieving the one or more objectives; and causing at least a portion of the personalized nutritional recommendation data to be displayed on a computing device associated with the individual.

18. The method of claim 17, wherein the health data includes one or more of microbiome data, long-term user data, or slow changing user data.

19. The method of claim 17, wherein causing the personalized nutritional recommendation data to be generated comprises determining that the one or more meals satisfy one or more constraints, wherein the constraints indicate one or more of a calorie constraint, a type of food constraint, or a favorite type of food constraint.

20. The method of claim 19, wherein the one or more objectives include a first objective to move a first value of the first target biomarker to a first target value and/or move a second value of the second target biomarker to a second target value.

21. The method of claim 17, wherein causing the personalized nutritional recommendation data to be generated comprises includes causing predication data for one or more foods indicated to be preferred by the individual to be generated.

22. The method of claim 17, wherein causing the personalized nutritional recommendation data to be generated includes causing prediction data to be generated for a plurality of foods associated with a plurality of meals.

23. The method of claim 17, wherein the health data includes first health data obtained in a structured setting and second health data obtained in a non-structured setting.

24. The method of claim 17, wherein the method further ranks foods indicated within the personal nutritional recommendation data and wherein causing the at least the portion of the personalized nutritional recommendation data to be displayed comprises causing a graphical user interface to be generated that includes a list of the ranked foods.

* * * * *